United States Patent

Cuberes-Altisent et al.

Patent Number: 5,182,280
Date of Patent: Jan. 26, 1993

[54] DERIVATIVES OF BENZIMIDAZOLE AND THEIR USE AS ANTIHISTAMINES

[75] Inventors: Maria R. Cuberes-Altisent; Jordi Frigola-Constansa; Juan Pares-Corominas, all of Barcelona, Spain

[73] Assignee: Laboratorios Del Dr. Esteve, S. A., Barcelona, Spain

[21] Appl. No.: 735,653

[22] Filed: Jul. 25, 1991

[30] Foreign Application Priority Data

Jul. 26, 1990 [FR] France .................... 90 09563

[51] Int. Cl.$^5$ .................... A61K 31/495; C07D 403/14
[52] U.S. Cl. .................... 514/252; 544/231; 544/366; 544/370
[58] Field of Search .................... 544/366, 370; 514/252

[56] References Cited

U.S. PATENT DOCUMENTS

| | | | |
|---|---|---|---|
| 3,247,202 | 4/1966 | Matter et al. | 544/366 |
| 4,200,641 | 4/1980 | Vandenberk et al. | 514/318 |
| 4,430,343 | 2/1984 | Iemura et al. | 544/370 |
| 4,603,130 | 7/1986 | Iemura et al. | 544/370 |
| 4,902,687 | 2/1990 | Ornstein | 544/366 |

FOREIGN PATENT DOCUMENTS

| | | |
|---|---|---|
| 139993 | 2/1988 | European Pat. Off. |
| 297661 | 1/1989 | European Pat. Off. |

OTHER PUBLICATIONS

Jilek et al., *Collect. Czech. Chem. Commun.* 53, p. 870 (1988).

*Drugs of the Future* (J. R. Prous, Ed.), VII, No. 10, pp. 711–779 (1982).

Primary Examiner—Mukund J. Shah
Assistant Examiner—E. Bernhardt
Attorney, Agent, or Firm—Dressler, Goldsmith, Shore, Sutker & Milnamow

[57] ABSTRACT

The present invention relates to novel compounds derived from benzimidazole, characterized in that they correspond to the formula I, or their therapeutically acceptable salts,

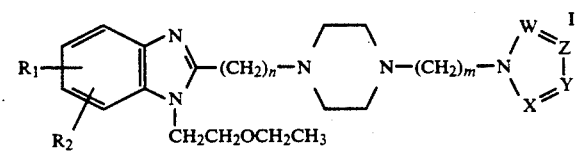

in which:

$R_1$ and $R_2$, equal or different, represent a hydrogen atom, a halogen, a lower alkyl radical, a hydroxy radical, an alkoxy radical, an alkyl carboxylate radical, an aryl or substituted aryl radical, n may have the values 0 or 1, m may have the values 2 to 4, X, Y, Z and W, equal or different, represents a nitrogen atom or a carbon atom bonded to a hydrogen atom, a halogen or another alkyl, aryl, alkoxycarbonyl, carboxy, hydroxyl, sulfonic and alkylsulfonic radical. The present invention relates also to the treatment of various allergic disorders caused by histamine.

4 Claims, No Drawings

DERIVATIVES OF BENZIMIDAZOLE AND THEIR USE AS ANTIHISTAMINES

BACKGROUND OF THE INVENTION

The present invention relates to novel derivatives of benzimidazole, their process of preparation as well as their use as medicaments.

The compounds according to the present invention correspond to the general formula I

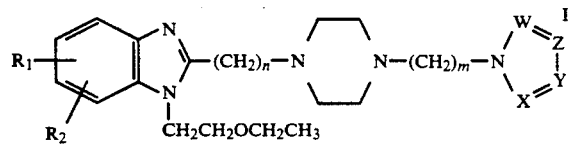

in which:

$R_1$ and $R_2$, equal or different, represent a hydrogen atom, a halogen, a lower alkyl radical, a hydroxy radical, an alkoxy radical, an alkyl carboxylate radical, an aryl or substituted aryl, n may have the values 0 or 1, m may have the values 2 to 4, X, Y, Z and W, equal or different, represent a nitrogen atom or a carbon atom linked to a hydrogen atom, a halogen or another alkyl, aryl, alkylcarbonyl, carboxy, hydroxyl, sulfo and alkylsulfonic radical.

In the scientific literature derivatives of benzimidazole are already known with different biological activities, like for example, analgesic and antiinflammatory activity (Japan Kokai 75, 126, 682), gastric antisecretory activity (EP 246,126 and EP 5129); antihistaminic activity (J. Jilek et al., Collect. Czech. Chem. Commun. 1988, 53, 870-83; U.S. Pat. No. 4,200,641; Drugs of the Future, VII; 10-1, 1982; R. Iemura et al., J. Med. Chem., 1987, 24, 31-37). The compounds according to the present invention are novel derivatives of benzimidazole, actually 1-(2-ethoxyethyl)-2-(alkylpiperazinylalkylazoles) benzimidazole. We have discovered that these novel derivatives have very good antihistaminic activity and they do not have side effects on the central nervous system.

The novel derivatives of general formula I may be prepared, according to the invention, according to any one of the following methods:

Method A

By reaction of the compound of the general formal IIa

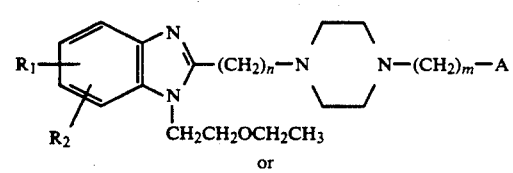

or

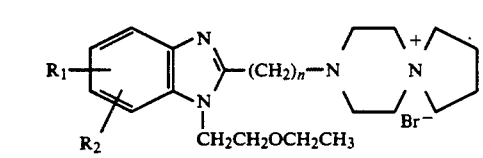

in which $R_1$, $R_2$, n and m have the previously mentioned meanings, and A represents a halogen atom or a good "starting group" selected from among tosyloxy or mesyloxy, with a compound of the general formula III

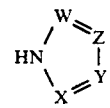

in which X, Y, Z and W have the previously mentioned meanings.

The reaction is performed in the presence of a suitable solvent, for example, dimethylsulfoxide, dimethylformamide, alcohols, hydrocarbons, aromatic or not, ethers, such as dioxane or diphenyl ether, or mixtures of these solvents. This reaction is advantageously conducted in the presence of a base such as hydroxides, carbonates or bicarbonates of alkali metals, or even a mixture of these bases. It is possible to employ also hydrides of alkali metals. The most suitable temperatures vary between room temperature and reflux temperature of the solvent, and the reaction time is comprised of between 1 hour and 24 hours.

Method B

By reaction of a compound of the general formula IIa, in which A represents an —$NH_2$ radical, with 2,5-dimethoxytetrahydrofuran.

The reaction is carried out in the presence of a suitable solvent, for example, acetic acid, water, alcohols, ketones or mixtures of these solvents. The most suitable temperatures vary between ambiant temperature and the reflux temperature of the solvent, and the reaction time is comprised between some minutes and 24 hours.

Method C

By reaction of a compound of a general formula IV

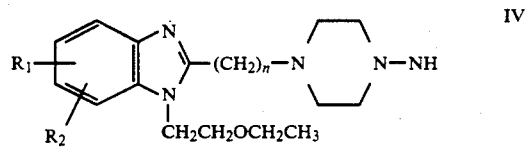

in which $R_1$, $R_2$ and n have the meanings indicated previously, with a compound of the general formula V

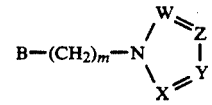

where X, Y, Z, W and m have the previously mentioned meanings, and B represents a halogen atom, or a good "starting group" selected from among tosyloxy or mesyloxy.

The reaction is carried out in the presence of a suitable solvent, for example, dimethylsulfoxide, dimethylformamide, alcohols, hydrocarbons, aromatic or not, ethers, dioxane or diphenyl ether, or mixtures of these solvents. This reaction is advantageously conducted in the presence of a base such as hydroxides, carbonates or bicarbonates of alkali metals, or even a mixture of these bases. The most suitable temperatures vary between room temperature and the reflux temperature of the solvent, and the reaction time is comprised of between 1 hour and 24 hours.

In the following examples the preparation of novel derivatives according to the invention is indicated. The examples below, given purely by way of illustration, must not however in any case, be taken as limiting the scope of the invention.

DESCRIPTION OF PREFERRED EMBODIMENTS

Method A

Example 1

Preparation of 1-(2-Ethoxyethyl)-2-4-[4--(4-bromopyrazol-1-yl)butyl]piperazin-1-ylmethyl benzimidazole.

a) 1-(2-Ethoxyethyl)-2-(8-methylaza-5-azoniaspiro [4,5] decane) benzimidazole bromide.

A mixture of 1.5 g (5.21 mmoles) of 1-(2-Ethoxyethyl)-2-(1-piperzinyl)benzimidazole, 1.41 g (6.5 mmoles) of 1,4-dibromobutane and 0.72 g (5.2 mmoles) of potassium carbonate in 50 ml of chloroform is placed under reflux for 16 hours. It was cooled, filtered and evaporated. The residue was triturated in ethyl ether and 2.1 g of 1-(2-Ethoxyethyl)-2-(8-methyloza-5-azoniaspiro [4.5] decane benzimidazole bromide was obtained, a hygroscopic solid which is used as such, without further purification.

$_1$H-NMR (CDCL$_3$): 1.05 (t,3H); 2.25 (m,4H); 3.25–4.15 (m,18H); 4.45 (t,2H); 7.27 (m,3H); 7.60 (m,1H).

b) 1-(2-Ethoxyethyl)-2-4-[4-(bromopyrazol-1-yl)butyl]piperazin-1-yl-methyl benzimidazole.

Under reflux, for 12 hours, a mixture of 2.3 g (5.44 mmoles) of 1-(2-Ethoxyethyl)-2-(8-methylaza-5-azoniaspiro [4.5] decane) benzimidazole bromide, 0.92 g (6.28 mmoles) of 4-bromo-1-H-pyrazole, 1.38 g (0.01 moles) of potassium carbonate and 30 ml of dimethylformamide were heated under reflux for 12 hours? It was cooled, filtered and the filtrate evaporated to dryness. The residue was taken up again with chloroform and it was washed with water. The organic phase was dried with Na$_2$SO$_4$, it was filtered and evaporated. The resulting oil was purified on a chromatographic silica column (eluant: chloroformmethanol 95:5). In this way 0.78 g of the compound was obtained in liquid form.

The spectroscopic data for its identification are shown in Tables 1 and 2.

Example 2

Preparation of 1-(2-Ethoxyethyl)-2-4-[4-(4-bromopyrazol1yl)butyl]-piperazinyl benzimidazole.

a) 1-(2-Ethoxyethyl)-2-(8-aza-5-azoniaspiro [4.5] decane)benzimidazole bromide.

The preparation is carried with the same procedure as that explained in example 1a.

$^1$H-NMR (CDCl$_3$): 1.08 (t,3H); 2.37 (m,4H); 3.42 (q,2H); 3.7–4.15 (m,14H); 4.32 (t,2H); 7.27 (m,3H); 7.60 (m,1H).

b) 1-(2-Ethoxyethyl)-2-4-[4-(-bromopyrazol-1-yl)butyl]-piperazinyl benzimidazole.

The preparation was carried out with the same method as example 1b.

The salt with maleic acid was prepared in ethanol and its melting point was 137°–139° C.

The spectroscopic data for its identification are shown in Tables 1 and 2.

Example 3

Preparation of 1-(2-Ethoxyethyl)-2-4-[4-(imidazol-1-yl)butyl]piperazin-1-ylmethyl benzimidazole.

The preparation is carried out in a manner quite similar to that explained for examples 1a and 1b.

The spectroscopic data for its identification are given in Tables 1 and 2.

Example 4

Preparation of 1-(2-Ethoxyethyl)-2-4-[4-(1,2,4-triazol-1-yl)butyl]piperazin-1-ylmethyl benzimidazole.

The preparation is carried out in a way quite similar to that explained in examples 1a and 1b.

The spectroscopic data for its identification are disclosed in Tables 1 and 2.

Example 5

Preparation of 1-(2-Ethoxyethyl)-2-4-[4-(4-sulfopyrazol-1-yl)butyl]piperazin-1-ylmethyl benzimidazole.

The preparation is carried out in a manner quite similar to that explained in examples 1a and 1b.

The spectroscopic data for its identification are shown in Tables 1 and 2.

Example 6

Preparation of 1-(2-Ethoxyethyl)-2-4-[4-(4-carboxypyrazol-1-yl)butyl]piperazin-1-ylmethyl benzimidazole.

According to the preparation explained in example 1a and 1b the 1-(2-Ethoxyethyl)-2-4-[4-(4-ethyloxycarbonylpyrazol-1-yl)butyl]piperazin-1-ylmethyl benzimidazole was obtained crude; it was purified on a chromatographic silica column (eluant: chloroformmethanol 95:5).

$^1$H-NMR (CDCl$_3$: 1.12 (t,3H); 1.45 (m,5H); 1.90 (m,2H); 2.44 (m,10H); 3.41 (q,2H); 3.60–3.86 (m,4H); 4.0–4.3 (m,4H); 4.50 (t,2H); 7.28 (m,3H); 7.75 (m,1H); 7.8 (s,2H). IR (film); 1715, 1560, 1470, 1225, 1120, 1040, 750 cm$^{-1}$ The salt with maleic acid was prepared in ethanol and its melting point was 114°–117° C.

The preceding ester as prepared was hydrolysed by treatment with a solution in ethanol, for 3 hours at ambient temperature, with 10% caustic soda. The alcohol is evaporated and the aqueous solution is neutralised with acetic acid. It was evaporated to dryness and the acid was extracted from the residue by digestion with dichloromethane.

In this way the corresponding acid was obtained, of which the spectroscopic data for it identification are shown in Tables 1 and 2.

Example 7

Preparation of 1-(2-Ethoxyethyl)-2-4-[4-(pyrazol-1-yl)butyl]piperazin-1-ylmethyl benzimidazole.

The preparation was carried out in a manner quite similar to that explained in examples 1a and 1b.

The salt with maleic acid was prepared in ethanol and melted at 112°–116° C.

The spectroscopic data for its identification are shown in Tables 1 and 2.

Example 9

Preparation of 1-(2-Ethoxyethyl)-2-4-[4-(4-carboxypryazol-1-yl)butyl]piperazine-1-yl benzimidazole.

According the preparation explained in examples 2a and 2b 1-(2-Ethoxyethyl)-2-4-[4-(4-ethyloxycarbonylpyrazol-1-yl)butyl]piperazin-1-yl benzimidazole was obtained crude, this was purified on a chromatographic column of silica (eluant: chloroform-methanol 95:5).

$^1$H-NMR (CDCl$_3$: 1.1 (t,3H); 1.3 (t,3H); 1.8 (m,4H); 2.15–2.7 (m,6H); 3.25 (m,6H); 3.7 (t,2H); 3.8–4.3 (m,6H); 7.2 (m,3H); 7.5 (m,1H); 7.8 (s,2H).

IR (KBr); 2950, 1715, 1220, 1125, 760 cm$^{-1}$

The previously prepared ester was hydrolysed by treatment with 10% caustic soda for 15 hours at room temperature, of a solution in ethanol. The alcohol was evaporated and the aqueous solution was neutralised with hydrochloric acid. It was evaporated to dryness and the acid was extracted from the residue by digestion with chloroform.

In this way the corresponding acid was obtained which was triturated with ethyl ether. The compound crystallizes in this solvent with a melting point of 145°–150° C.

The spectroscopic data for its identification are given in Tables 1 and 2.

Example 10

Preparation of 1-(2-Ethoxyethyl)-2-4-[4-(4,5-dichloroimidazol-1-yl]piperazin-1-yl-methyl benzimidazole.

The preparation was carried out in a manner quite similar to that explained in examples 1a and 1b.

The salt with fumaric acid was prepared in ethanol and melted at 123°–130° C.

The spectroscopic datas for its identification are shown in Tables 1 and 2.

Method B

Example 8

Preparation of 1-(2-Ethoxyethyl)-2-4-[4-(pyrrol-1-yl)butyl]piperazin-1-yl-methyl benzimidazole.

a) 1-(2-Ethoxyethyl)-2-4-(4-aminobutyl)-1-yl-methyl benzimidazole.

There was put under reflux for 3 hours a mixture of 6.4 g (22 mmoles) of 1-(2-Ethoxyethyl)-2-(1-methylpiperazinyl)benzimidazole, 6.25 g (22 mmoles) of N-(4-bromobutyl) phthalimide, 4.55 g (33 mmoles) of potassium carbonate and 4.62 g (30 mmoles) of sodium iodide in 100 ml of methyl ethyl ketone. It was cooled, filtered and the filtrate evaporated to dryness. The residue is taken up again with chloroform and with water. The organic base was dried with Na$_2$SO$_4$, it was filtered and evaporated under vacuum. The resulting oil was purified on a chromatographic silica column (eluant: chloroformemethanol 95:5). In this way there were obtained 8.47 g of 1-(2-Ethoxyethyl)-2-4-(4-N-phthalimidobutyl)piperazin-1-yl-methyl benzimidazole.

$_1$NMR (CDCl$_3$: 1.1 (t,3H); 2.6 (m,4H); 2.45 (m,10H); 3.3 (q,2H); 3.5–3.8 (m,6H); 4.4 (t,2H); 7,15 (m,4H); 7.55 (m,4H).

Under reflux for 2 hours were heated a solution of 8.46 g (17.3 mmoles) of the compound previously obtained at 1.73 g (34.6 mmoles) of hydrazine hydrate in 150 ml of ethanol. It was cooled, filtered, washed with ethanol and the filtrate evaporated to dryness under vacuum. The residue was taken up with chloroform and washed with water, and dried, evaporated and 4.35 g of 1-(2-Ethoxyethyl)-2-4-(4-aminobutyl)piperazin-1-yl-methyl benzimidazole obtained which were used in another purification.

$^1$H-NMR (CDCl$_3$): 1.1 (t,3H); 1.45 (m,4H); 1.75 (s,2H); 2.05–2.75 (m,12H); 3.35 (q,2H); 3.6–3.9 (m,4H); 4.45 (t,2H); 7.20 (m,3H); 7.6 (m,1H).

b) 1-(2-Ethoxyethyl)-2-4-[4-(pyrrol-1-1yl)butyl]piperazin-1-ylmethyl benzimidazole.

Under reflux, for 20 minutes, there was heated a solution of 2 g (5.57 mmoles) of 1-(2-Ethoxyethyl)-2-4-(-aminobutyl)-piperazin-1-yl-methyl benzimidazole and 0.735 g (5.57 mmoles) of 2.5-dimethoxytetrahydrofurane in 20 ml of acetic acid, poured over ice water, neutralized with Na$_2$HCO$_3$ and extracted iwth chloroform. It was dried with Na$_2$SO$_4$, and evaporated under vacuum to dryness. In this way 2.75 g of the crude compound was obtained which was purified on a Chromatographic silica column (eluant: chloroformemethanol 94:6).

The salt with fumaric acid was prepared in ethanolethyl ether, with a melting point of 138°–142° C.

The spectroscopic data for its identification are given in Tables 1 and 2.

Method C

Example 6

Preparation of 1-(2-Ethoxyethyl)-2-4-[4-(4-carboxypyrazol-1-yl)butyl]piperazin-1-ylmethyl benzimidazole.

There was placed under reflux for 4 hours a mixture of 5 g (17.36 mmoles) of 1-(2-Ethoxyethyl)-2-(1-methylpiperazinyl) benzimidazole, 4.77 g (17.36 mmoles) of 1-(4-bromobutyl)-4-pyrazole of ethyl carboxylate, 3.52 g (26 mmoles of potassium carbonate and 3.52 g (23.5 mmoles) of sodium iodide in 100 ml of methyl ethyl ketone. It was cooled, filtered and the filtrate evaporated to dryness. The residue was taken up again with chloroform and. with water, the organic phase with Na$_2$SO$_4$, it was filtered and evaporated under vacuum. The resultant crude product was purified on a chromatographic silica column (eluant: chloroformmethanol 95:5) and in this way 4.85 g of 1-(2-Ethoxyethyl)-2-4-[4-(4-ethyloxycarbonylpyrazol-1-yl)butyl]piperazin-1-yl-methyl benzimidazole was obtained.

The spectroscopic data of the compound are the same already given in example 6 of method A.

This ester was hydrolysed similarly to the method explained in example 6 of method A and the acid obtained with the spectroscopic data explained in Tables 1 of 2.

Example 8

Preparation of 1-(2-Ethoxyethyl)-2-4-[4-(pyrrol-1-yl)butyl]piperazin-1-ylmethyl benzimidazole.

The preparation is carried out in a manner quite similar to that explained in the preceding example, and the compound of salt with fumaric acid has a melting point of 137°–142° C. was obtained.

The spectroscopic data for its identification was explained in Tables 1 and 2.

Pharmacological Activity

The products according to the present invention are powerful antihistaminics and are characterized by the fact that they are free from sedative effects, contrary to the majority of the known antihistaminics.

"In vivo" Antihistaminic Activity

The antihistaminic activity was studied by determining the protection in the face of the mortality induced by the product 48/80 in the rat. This test was realized in accordance with the technique described by C. J. E. Niemegeers and cols. (*Arch, int. Pharmacodyn.* 234, 164–176 (1978)).

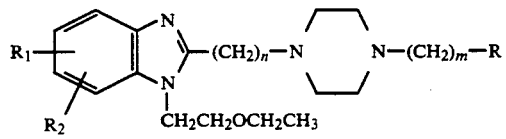

| Example n° | $R_1$ | $R_2$ | n | m | R | Méthode | IR (cm$^{-1}$) (film) |
|---|---|---|---|---|---|---|---|
| 1 | H | H | 1 | 4 | −N⟨pyrrole⟩−Br | A | 2937, 2808, 1465, 1117, 952, 747 |
| 2 | H | H | 0 | 4 | −N⟨pyrrole⟩−Br | A | maleate (KBr): 2975, 2881, 1706, 1619, 1475, 1356, 862, 744, 650 |
| 3 | H | H | 1 | 4 | −N⟨pyrrole⟩ | A | 2938, 2812, 1463, 1132, 749, 665 |
| 4 | H | H | 1 | 4 | −N⟨imidazole⟩ | A | 2940, 2812, 1673, 1463, 1332, 1136, 1011, 749 |
| 5 | H | H | 1 | 4 | −N⟨pyrrole⟩−SO$_3$H | A | 3600–2800, 1662, 1464, 1220, 1183, 1129, 1052, 670 |
| 6 | H | H | 1 | 4 | −N⟨pyrrole⟩−CO$_2$H | A, C | 3600–3200, 2931, 1706, 1462, 1119, 756 |
| 7 | H | H | 1 | 4 | −N⟨pyrrole⟩ | A | 2838, 2825, 1512, 1462, 1125, 913, 731 |
| 8 | H | H | 1 | 4 | −N⟨pyrrole⟩ | B, C | 2970, 1643, 1463, 1416, 1332, 1120, 749 |
| 9 | H | H | 0 | 4 | −N⟨pyrrole⟩−CO$_2$H | A | 3360–3150, 2944, 1700, 1525, 1469, 1412, 1125, 750 |

-continued

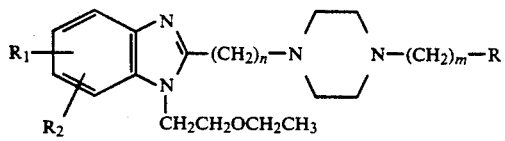

| Example $n^o$ | $R_1$ | $R_2$ | n | m | R | Méthode | IR (cm$^{-1}$) (film) |
|---|---|---|---|---|---|---|---|
| 10 | H | H | 1 | 4 | 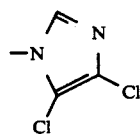 | A | 2940, 2810, 1463, 1254, 749, 666 |

TABLEAU 2

| Example $n^o$ | $^1$H-RMN (CDCl$_3$) δ |
|---|---|
| 1 | 1,12 (t,3H); 1,46 (m,2H); 1,81 (m,2H); 2,45 (m,10H); 3,41 (q,2H); 3,81 (m,4H); 4,08 (t,2H); 4,50 (t,2H); 7,33 (m,5H); 7,69 (m,1H) |
| 2 | 1,13 (t,3H); 1,60 (m,2H); 1,87 (m,2H); 2,55 (t,2H); 2,76 (m,4H); 3,44 (m,6H); 3,81 (t,2H); 4,12 (dt,4H); 7,12–7,61 (m,6H) |
| 3 | 1,12 (t,3H); 1,70 (m,4H); 2,35 (m,10H); 3,40 (q,2H); 3,75 (m,6H); 4,35 (t,2H); 6,9 (s,1H); 7,0 (s,1H); 7,18–7,45 (m,4H); 7,7 (m,1H) |
| 4 | 1,13 (t,3H); 1,46 (m,2H); 1,90 (m,2H); 2,45 (m,10H); 3,42 (q,2H): 3,76 (t,2H); 3,88 (s,2H); 4,20 (t,2H); 4,52 (t,2H); 7,30 (m,3H); 7,71 m,1H); 7,94 (s,1H); 8.06 (s,1H) |
| 5 | d$_6$-DMSO 1,0(t,3H); 2,11 (m,4H); 3,67 (m,16H); 4,37 (t,2H); 4,65 (t,2H); 7,7 (m,6H) |
| 6 | 1,10 (t,3H); 1,58 (m,2H); 1,86 (m,2H); 2,68 (m,10H); 3,38 (q,2H); 3,73 (t,2H); 3,89 (s,2H); 4,15 (t,2H); 4,48 (t,2H); 7,27 (m,3H); 7,84 (m,3H) |
| 7 | 1,12 (t,3H); 1,50 (m,2H); 1,85 (m,2H); 2,45 (m,10H); 3,41 (q,2H); 3,75 (t,2H); 3,87 (s,2H); 4,14 (t,2H); 4,50 (t,2H); 6,22 (m,1H); 7,19–7,47 (m,6H) |
| 8 | 1,1 (t,3H); 1,70 (m,4H); 2,69 (m,10H); 3,40 (q,2H); 3,55–3,90 (m,6H); 4,46 (t,2H); 6,12 (m,2H); 6,62 (m,2H); 7,1–7,7 (m,4H) |
| 9 | 1,14 (t,3H); 1,59 (m,2H); 1,90 (m,2H); 2,4–2,8 (m,6H); 3,3–3,6 (m,6H); 3,83 (t,2H); 4,17 (dt,4H) |
| 10 | 1,12 (t,3H); 1,55 (m,2H); 1,80 (m,2H); 2,1–2,6 (m,10H); 3,41 (q,2H); 3,86 (m,6H); 4,49 (t,2H); 7,29 (m,4H); 7,75 (m,1H) |

The products according to the present invention are administered i.p. to rats. After 60 minutes the compound 48/80 is administered (0.5 mg/kg, i.v.). The protective activity is defined as the survival of the rats 4 hours after the i.v. injection of 48/80.

The activity of the products at several doses in order to determine the dose capable of protecting 50% of the animals (ED-50) was studied.

Then the antihistaminic activity of several of the products according to the present patent application are summarized. This activity is compared with that of difenhidramine, a reference antihistaminic agent. The majority of the products according to the present invention are much more active than difenhidramine, considering that their ED-50 is much smaller.

| "In vivo" Antihistaminic Activity: Protection from death induced by 48/80 | |
|---|---|
| Example no. | ED-50 (mg/kg, i.p.) |
| 1 | 0.09 |
| 2 | 2.7 |
| 3 | 0.13 |
| 4 | 0.036 |
| 5 | 2.6 |
| 6 | 0.064 |
| 7 | 0.02 |
| 8 | 0.02 |
| 9 | 0.84 |
| 10 | 0.66 |
| Difenhidramine | 0.84 |

Sedative Effect: 1) Irwin Test

To study the sedative effect of the products according to the present invention, they are administered to rats i.p. and the behavior of the animals is observed, following the standards described in the test of S. Irwin (*Science*, 136, 123–128 (1962)).

The results obtained in the two evaluations which reflect the sedative action are collected below:

Pas.: Passivity, sedation, prostration. Quantitative evaluation between 0 and 3. They were performed 1, 2 and 3 hours after the treatment.

Atax.: Ataxia, the alterations in coordination in locomotion were evaluated. They were evaluated between 0 and 3. They were performed 1, 2 and 3 hours after the treatment.

Below are summarized the results of the study of the sedative action of some of the products according to the present invention, by way of example. This activity was compared with that of difenhidramine, reference antihistamine. The products according to the present invention have shown very slight sedative action, contrary to difenhidramine which is established to be toxic at the dose of 80 mg/kg, i.p., on account of CNS depressor effects.

| Sedative Effect: 1) Irwin Test | | | |
|---|---|---|---|
| | Dose | Effect | |
| Example No. | (mg/kg) | Pas. | Atax. |
| 1 | (80) | 1.4 | 1.3 |
| 2 | (40) | 0 | 0.4 |
| | (80) | 0.7 | 1.3 |
| 3 | (80) | 0 | 0 |
| 4 | (80) | 0.4 | 0.5 |
| 5 | (80) | 0.4 | 0.4 |
| 6 | (80) | 0 | 0 |
| 7 | (80) | 0 | 0 |
| | (160) | 0 | 0.3 |

-continued

| Sedative Effect: 1) Irwin Test | | | |
|---|---|---|---|
| | Dose | Effect | |
| Example No. | (mg/kg) | Pas. | Atax. |
| 8 | (80) | 0 | 0 |
| 9 | (80) | 0 | 0 |
| Difenhidramine | (40) | 0 | 0.9 |
| | (80) | | Toxic |

Sedative Effect: 2) Potentiation of the sleep time induced by pentobarbital.

Study of the potentiation of the sleep time due to pentobarbital was carried out by following the method described by L. E. Allen and cols. (*Arz. Forsch.* 24, (6), (1974)). The products studied were administered orally. One hour later the sodium pentobarbital was administered (35 mg/kg, s.c.) and the time the animals are delayed in waking up is determined. The sleep time was compared with a group of control animals, treated only with sodium pentobarbital.

In order to complete the studies which demonstrate the absence of sedative action of the products according to the present invention, in this test the activity of one of the most powerful products was compared with a lesser sedative effect (example 7) with the reference antihistamine, difenhidramine. Below are given the results of this test with example 7 and difenhidramine. It is obvious that difenhidramine potentiates significantly the sleep time at the dose of 20 mg/kg, whilst example 7 does not potentiate the sleep time induced by pentobarbital even at 320 mg/kg, the maximum dose tested.

| Sedative Effect: 2) Potentiation of the sleep time induced by pentobarbitol | | |
|---|---|---|
| Example No. | Dose (mg/kg, orally) | Potentiation of sleep time |
| 7 | 80 | 10% N.S. |
| | 160 | 11% N.S. |
| | 320 | 22% N.S. |
| Difenhidramine | 10 | 22% N.S. |
| | 20 | 38% * |

N.S.: Not significant
*: Significant difference with the control group (p < 0.05)

Below will be indicated by way of example, a particular galenic form of the deritatives according to present invention.

| Tablets | |
|---|---|
| Formula per Tablet | |
| Example No. 7 | 10.00 mg |
| Lactose | 54.00 mg |
| Cornstarch | 26.00 mg |
| Microcrystallline cellulose | 18.00 mg |
| Polyvinylpyrrolidone | 6.00 mg |
| Sodium croscarmellose | 3.60 mg |
| Colloidal sillicic dioxide | 0.60 mg |
| Magnesium stearate | 1.20 mg |

We claim:

1. Compounds derived from benzimidazole characterized in that they correspond to the formula I, or their therapeutically acceptable salts,

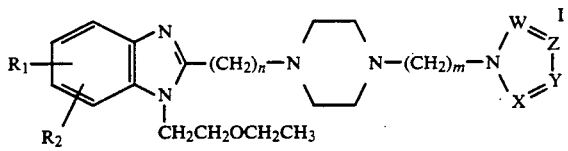

in which, $R_1$ and $R_2$, equal or different, represent a hydrogen atom, a halogen, a lower alkyl radical or a hydroxy radical, n can have the values 0 or 1, m can have the values 2 to 4, X, Y, Z and W are equal or different, and represent a nitrogen atom or a carbon atom bonded to a hydrogen atom, to a halogen or to another lower alkyl, alkoxycarbonyl having up to two carbon atoms in its alkyl group, carboxy, hydroxyl or sulfo radical.

2. The compounds selected from the following group:

1-(2-Ethoxyethyl)-2-{4-[4-(4-bromopyrazol-1-yl)butyl]piperazin-1-yl-methyl}benzimidazole;

1-(2-Ethoxyethyl)-2-{4-[4-(4-bromopyrazol-1-yl)butyl]piperazinyl}benzimidazole;

1-(2-Ethoxyethyl)-2-{4-[4-(imidazol-1-yl)butyl]piperazin-1-yl-methyl}benzimidazole;

1-(2-Ethoxyethyl)-2-{4-[4-(1,2,4-triazol-1-yl)butyl]piperazin-1-yl-methyl}benzimidazole;

1-(2-Ethoxyethyl)-2-{4-[4-(4-sulfopyrazol-1-yl)butyl]piperazin-1-yl-methyl}benzimidazole;

1-(2-Ethoxyethyl)-2-{4-[4-(4-carboxypyrazol-1-yl)butyl]piperazin-1-yl-methyl}benzimidazole;

1-(2-Ethoxyethyl)-2-{4-[4-(4-ethyloxycarbonylpyrazol-1-yl)butyl]piperazin-1-yl-methyl}benzimidazole;

1-(2-Ethoxyethyl)-2-{4-[4-(pyrazol-1-yl)butyl]piperazin-1-yl-methyl}benzimidazole;

1-(2-Ethoxyethyl)-2-{4-[4-(pyrrol-1-yl)butyl]piperazin-1-yl-methyl}benzimidazole;

1-(2-Ethoxyethyl)-2-{4-[4-(4-carboxypyrazol-1-yl)butyl]piperazin-1-yl}benzimidazole;

1-(2-Ethoxyethyl)-2-{4-[4-(4-ethyloxycarbonylpyrazol-1-yl)butyl]piperazin-1-yl}benzimidazole;

1-(2-Ethoxyethyl)-2-{4-[4-(4,5-dichloroimidazol-1-yl)butyl]piperazin-1-yl-methyl}benzimidazole.

3. Pharmaceutical compositions, characterized by the fact that they contain, besides a pharmaceutically acceptable support, at least one derivative of the formula I or one of its physiologically acceptable salts, according to one of claims 1 or 2.

4. Method of prophylaxis and of treating various allergic disorders caused by histamine, utilizing a derivative of formula I or its physiologically acceptable salts, according to one of claims 1 or 2.

* * * * *